(12) United States Patent
Kohara et al.

(10) Patent No.: US 7,666,662 B2
(45) Date of Patent: Feb. 23, 2010

(54) CHEMICAL REACTION DEVICE, CHEMICAL REACTION SYSTEM AND CHEMICAL REACTION METHOD

(75) Inventors: Yoshinobu Kohara, Kokubunji (JP); Kazunori Okano, Shiki (JP); Hideyuki Noda, Kokubunji (JP)

(73) Assignee: Hitachi, Ltd., Tokyo (JP)

( * ) Notice: Subject to any disclaimer, the term of this patent is extended or adjusted under 35 U.S.C. 154(b) by 679 days.

(21) Appl. No.: 10/854,018

(22) Filed: May 26, 2004

(65) Prior Publication Data

US 2005/0014246 A1 Jan. 20, 2005

(30) Foreign Application Priority Data

Jul. 14, 2003 (JP) .............................. 2003-196178

(51) Int. Cl.
*C12M 1/34* (2006.01)
(52) U.S. Cl. .................................................. 435/287.1
(58) Field of Classification Search ........................ None
See application file for complete search history.

(56) References Cited

U.S. PATENT DOCUMENTS

| 4,438,075 | A | * | 3/1984 | von Branchel et al. | ...... | 422/189 |
| 5,009,849 | A | | 4/1991 | Ebner et al. | | |
| 6,663,833 | B1 | * | 12/2003 | Stave et al. | ...... | 422/81 |

FOREIGN PATENT DOCUMENTS

| JP | 11-75812 | 8/1997 |
| JP | 11-243997 | 3/1998 |
| JP | 2003-315336 | 4/2002 |
| WO | WO 01/09389 A2 | 2/2001 |

OTHER PUBLICATIONS

Nielsen et al., "Novel Tubing Microreactor for Monitoring Chemical Reactions", Analytical Chemistry, vol. 74, No. 13, Jul. 1, 2002, pp. 3112-3117.

Tokeshi et al., "Determination of Subyoctomole Amounts of Nonfluorescent Molecules Using a Thermal Lens Microscope: Subsingle-Molecule Determination", Analytical Chemistry, vol. 73, No. 9, May 1, 2001, pp. 2112-2116.

Schena et al, "Quantitative Monitoring of Gene Expression Patterns with a Complementary DNA Microarray", Science, vol. 270, Oct. 20, 1995, pp. 467-469.

Fodor et al., "Light-Directed, Spatially Addressable Parallel Chemical Synthesis", Research Article, Feb. 15, 1991, pp. 767-773.

Arenkov et al., "Protein Microchips: Use for Immunoassay and Enzymatic Reactions", Analytical Biochemistry, Jun. 7, 1999, pp. 123-131.

Hong et al., "Integration of Gene Amplification and Capillary Gel Electrophoresis on a Polydimethlysiloxane-glass Hybrid Microchip", Electrophoresis 2001, vol. 22, pp. 328-333.

* cited by examiner

*Primary Examiner*—Ann Y Lam
(74) *Attorney, Agent, or Firm*—Stites & Harbison PLLC; Juan Carlos A. Marquez, Esq.

(57) ABSTRACT

A chemical reaction device is provided for a chemical reaction between molecules immobilized on a solid phase and molecules in a solution, and a chemical analysis device is also provided to capture molecules in the solution by molecules immobilized on the solid phase through a chemical reaction and subsequent measurement of the captured molecules. Reaction efficiency as well as sample throughput are thereby improved. The chemical reaction device and the chemical analysis device use a channel of a microfluidic device for a reaction vessel, and at least a particular molecule is immobilized on an interior surface and a fixed structure or a non-fixed obstacle against a flow is provided in the channel. In a typical reaction vessel having an enzyme immobilized on an interior surface of a capillary and glass beads functioning as an obstacle for the flow filled in the channel of the capillary, a reaction solution can move either in one direction or back and forth in two directions to thereby undergo a reaction with the enzyme immobilized on the interior surface. The flow of the reaction solution is not a laminar flow so that a reaction between the particular molecule immobilized and the reaction solution proceeds at high efficiency.

10 Claims, 7 Drawing Sheets

```
                         SEQUENCE LISTING

<160> NUMBER OF SEQ ID NOS: 20

<210> SEQ ID NO 1
<211> LENGTH: 18
<212> TYPE: DNA
<213> ORGANISM: Homo sapiens

<400> SEQUENCE: 1
tgtcaccgtc gtggaaag                                                  18

<210> SEQ ID NO 2
<211> LENGTH: 18
<212> TYPE: DNA
<213> ORGANISM: Homo sapiens

<400> SEQUENCE: 2
atctgactgc ggctcctc                                                  18

<210> SEQ ID NO 3
<211> LENGTH: 18
<212> TYPE: DNA
<213> ORGANISM: Homo sapiens

<400> SEQUENCE: 3
aagaagccca gacggaaa                                                  18

<210> SEQ ID NO 4
<211> LENGTH: 18
<212> TYPE: DNA
<213> ORGANISM: Homo sapiens

<400> SEQUENCE: 4
gcctcacaac ctccgtca                                                  18
```

```
<210> SEQ ID NO 5
<211> LENGTH: 18
<212> TYPE: DNA
<213> ORGANISM: Homo sapiens

<400> SEQUENCE: 5
tcatagggca ccaccaca                                                 18

<210> SEQ ID NO 6
<211> LENGTH: 18
<212> TYPE: DNA
<213> ORGANISM: Homo sapiens

<400> SEQUENCE: 6
atgatggtga ggatgggc                                                 18

<210> SEQ ID NO 7
<211> LENGTH: 18
<212> TYPE: DNA
<213> ORGANISM: Homo sapiens

<400> SEQUENCE: 7
ccctttcttg cggagctt                                                 18

<210> SEQ ID NO 8
<211> LENGTH: 18
<212> TYPE: DNA
<213> ORGANISM: Homo sapiens

<400> SEQUENCE: 8
tttcttcttt ggctgggg                                                 18

<210> SEQ ID NO 9
<211> LENGTH: 18
<212> TYPE: DNA
<213> ORGANISM: Homo sapiens

<400> SEQUENCE: 9
cctgggcatc cttgagtt                                                 18

<210> SEQ ID NO 10
<211> LENGTH: 18
<212> TYPE: DNA
<213> ORGANISM: Homo sapiens

<400> SEQUENCE: 10
atggcgggag gtagactg                                                 18

<210> SEQ ID NO 11
<211> LENGTH: 18
<212> TYPE: DNA
<213> ORGANISM: Homo sapiens

<400> SEQUENCE: 11
ctttccacga cggtgaca                                                 18

<210> SEQ ID NO 12
<211> LENGTH: 18
<212> TYPE: DNA
<213> ORGANISM: Homo sapiens

<400> SEQUENCE: 12
gaggagccgc agtcagat                                                 18
```

```
<210> SEQ ID NO 13
<211> LENGTH: 18
<212> TYPE: DNA
<213> ORGANISM: Homo sapiens

<400> SEQUENCE: 13
tttccgtctg ggcttctt                                                   18

<210> SEQ ID NO 14
<211> LENGTH: 18
<212> TYPE: DNA
<213> ORGANISM: Homo sapiens

<400> SEQUENCE: 14
tgacggaggt tgtgaggc                                                   18

<210> SEQ ID NO 15
<211> LENGTH: 18
<212> TYPE: DNA
<213> ORGANISM: Homo sapiens

<400> SEQUENCE: 15
tgtggtggtg ccctatga                                                   18

<210> SEQ ID NO 16
<211> LENGTH: 18
<212> TYPE: DNA
<213> ORGANISM: Homo sapiens

<400> SEQUENCE: 16
gcccatcctc accatcat                                                   18

<210> SEQ ID NO 17
<211> LENGTH: 18
<212> TYPE: DNA
<213> ORGANISM: Homo sapiens

<400> SEQUENCE: 17
aatctccgca agaaaggg                                                   18

<210> SEQ ID NO 18
<211> LENGTH: 18
<212> TYPE: DNA
<213> ORGANISM: Homo sapiens

<400> SEQUENCE: 18
ccccagccaa agaagaaa                                                   18

<210> SEQ ID NO 19
<211> LENGTH: 18
<212> TYPE: DNA
<213> ORGANISM: Homo sapiens

<400> SEQUENCE: 19
aactcaagga tgcccagg                                                   18

<210> SEQ ID NO 20
<211> LENGTH: 18
<212> TYPE: DNA
<213> ORGANISM: Homo sapiens

<400> SEQUENCE: 20
cagtctacct cccgccat                                                   18
```

CHEMICAL REACTION DEVICE, CHEMICAL REACTION SYSTEM AND CHEMICAL REACTION METHOD

CROSS-REFERENCE TO RELATED APPLICATIONS

This application is related to U.S. application Ser. No. 10/750,886 filed on Jan. 5, 2004, U.S. application Ser. No. 10/788,440 filed on Mar. 1, 2004, and U.S. application Ser. No. 10/790,063 filed on Mar. 2, 2004, the disclosures of which are hereby incorporated by reference.

CLAIM OF PRIORITY

The present application claims priority from Japanese application JP 2003-196178 filed on Jul. 14, 2003, the content of which is hereby incorporated by reference into this application.

FIELD OF THE INVENTION

This invention relates a chemical reaction device, a chemical reaction system, and a chemical reaction method. More specifically, this invention relates to a chemical reaction device, a chemical reaction system, and a chemical reaction method wherein a chemical reaction in a minute space is utilized. This invention also relates to a chemical reaction device, a chemical reaction system, and a chemical reaction method wherein a biological molecule such as a nucleic acid or a protein is involved in the reaction.

BACKGROUND OF THE INVENTION

Recent years have seen significant advances in the technology of constituting a minute space for conducting a chemical reaction in such a space. One method of constituting such a minute space is use of photolithography which is a technology most frequently used in the production of a semiconductor. A microfluidic device can be constituted by forming a groove in a silicon substrate by means of photolithographic process, and adhering another substrate over the groove to thereby form a minute channel for receiving a fluid which is actuated by the device. Various proposals have been made for use of such microfluidic device in chemical production (for example, Analytical Chemistry, 74, 3112-3117 (2002)) and chemical analysis (for example, Analytical Chemistry, 73, 2112-2116 (2001)).

Chemical reactions utilizing an enzyme immobilized on microparticles have been investigated for various enzymatic reactions, and typical processes include the process wherein microparticles having an enzyme immobilized thereon are suspended in the solution for chemical reaction, and the process wherein such microparticles are used by filling in a column having a diameter much larger than the microparticles. Also known in the art as a process utilizing a chemical reaction that takes place at the interface between the microparticle and the liquid is the purification of a particular molecule by using microparticles wherein microparticles having immobilized protein A or the like are filled in a column for use as an antibody purification column.

In the meanwhile, biological molecules are typically measured by immobilizing a probe molecule in each well of a micro-well plate, and dispensing the sample in each well to measure the biological molecule captured by the probe molecule. In the case of ELISA, for example, an antibody is used for the probe molecule to quantitatively measure the biological molecule in the sample. In this case, an antibody molecule which has affinity for the biological molecule is immobilized on the plate, and after capturing the biological molecule by the antibody molecule, a high sensitivity measurement by enzymatic chemiluminescence is conducted using an enzyme-labeled secondary antibody having affinity for the biological molecule.

Another method for measuring a biological molecule that is in development is a method wherein a plurality of probe molecules are immobilized in different areas of the solid phase to measure the biological molecule captured by each probe molecule. An example is the DNA chip wherein a plurality of probe DNAs are immobilized on a planar substrate of glass or the like for detection of nucleic acid molecules. In the case of this chip, a solution containing a fluorescence-labeled nucleic acid molecule is placed on the chip for hybridization and the amount of analyte nucleic acid molecule in the solution is determined by detecting fluorescence on the chip. The methods often used for producing such a DNA chip include spotting of the DNA probe on a slide glass (for example, Science, 270, 467-470 (1995)), and use of a photolithographic process and the sequential synthesis of the DNA by a photochemical reaction (for example, Science, 251, 767-773 (1991)). Also proposed is a protein chip wherein a plurality of proteins are simultaneously measured (for example, Analytical Biochemistry, 278, 123-131 (2000)). Devices using not the planar surface but a channel formed in the device have also been proposed, and exemplary such devices include the one wherein a DNA probe has been immobilized in the capillary (for example, Japanese Patent Application Laid-Open No. 11-75812), and a probe array wherein probe-conjugated microparticles have been arranged in the interior of the capillary (for example, Japanese Patent Application Laid-Open No. 11-243997).

Processing a large amount of sample in a short time is generally difficult in the chemical reaction system where molecules immobilized on the solid phase are reacted with the molecules in the solution, or in the chemical analysis system where molecules immobilized on the solid phase capture the molecules in the solution by chemically reacting with such molecules and the captured molecules are measured. To be more specific, the methods mentioned in the Prior Art section including the method wherein microparticles are filled in a column, the method using a micro-well plate, and the method using a DNA chip have been associated with the difficulty of establishing the sample flow while promoting reaction in the minute space, and as a consequence, improvement in the chemical reaction efficiency and reduction of the process time have been difficult.

SUMMARY OF THE INVENTION

In view of the problems to be obviated by the present invention as described above, the present invention attempts to increase the reaction efficiency and reduce the reaction time in the chemical reaction where molecules immobilized on the solid phase are reacted with the molecules in the solution, or in the chemical analysis where molecules immobilized on the solid phase capture the molecules in the solution by chemically reacting with such molecules and the captured molecules are measured. Another object of the present invention is to improve the throughput to thereby increase the reaction efficiency when the sample is the one at a low concentration.

In the case of a minute space, an efficient and uniform chemical reaction can be expected since the space where molecules involved in the chemical reaction can move by molecular diffusion is limited and probability of the contact between the molecules is increased. Use of a small space also enables reduction in the amount of the chemical reagent and the waste produced, as well as loss of the sample.

Accordingly, improvement of the reaction efficiency by using a microfluidic device is contemplated wherein the micro-space in the channel is used for the reaction space, and wherein a particular molecule involved in the reaction is immobilized in the channel. When a narrow channel is used in such a case, the time of the solution passing over the area where the particular molecule has been immobilized will be reduced and diffusion of the reactant molecules in the solution will be insufficient, presumably resulting in the difficulty of realizing sufficient reaction efficiency. On the other hand, a decrease in the flow rate to allow a sufficient time for the diffusion to thereby increase the reaction efficiency would be associated with the risk of reduced sample throughput.

In order to improve such a situation, the present invention provides a chemical reaction device, a chemical reaction system, and a chemical reaction method wherein a channel is used for the space of the chemical reaction, and wherein a particular molecule is immobilized in its interior surface, and a structure or a flow obstacle is placed in the channel. This structure or obstacle creates turbulence in the flow of the sample solution through the microfluidic device which is normally a laminar flow to remarkably increase the substantial diffusion coefficient of the molecules in the solution, and as a consequence, a dramatic increase in the reaction efficiency can be attained with no compromise in the sample throughput. The time required for the reaction and analysis is also reduced, and handling of a sample at a low concentration is also enabled.

The chemical reaction device according to the present invention has a characteristic feature that it has a channel for receiving the solution and the structure accommodated in the channel, and a particular molecule which reacts with a substance included in a solution is immobilized in the interior surface or lumen wall of the channel. The structure may have a diameter which is in the range of 30 to 90% of the diameter of the channel, and when volume allowed for the sample to flow in the channel is V1, and interior volume of the channel is V2, the ratio V1/V2 may be in the range of 0.4 to 0.95. The structure may be a fine particle or a strip, and the strip may be a wire or a rod. In the channel within the chemical reaction device, the flow of the solution may be at least partly a turbulent flow. The channel may be constituted from a groove formed in a first substrate and a second substrate disposed to cover the groove, or alternatively, the channel may be a lumen of a capillary.

The chemical reaction system according to the present invention comprises a thermal chamber for placing a reaction device for accommodating a solution and a structure, and an introducer for introducing the solution into the reaction device. The reaction device has a molecule immobilized on its interior surface to allow a chemical reaction to take place between the immobilized molecule and the substance included in the solution introduced by the solution introducer. The chemical reaction system may further comprise a detector for detecting the reaction that takes place in the reaction device.

Furthermore, the chemical reaction method according to the present invention comprises the steps of: preparing a reaction device having a particular molecule immobilized on its interior surface, and having a structure accommodated in its interior; introducing a solution into the reaction device; and allowing the particular molecule immobilized on the interior surface to undergo a chemical reaction with a molecule included in the solution; wherein, in the step of chemical reaction, the solution moves in relation to the structure. In this chemical reaction method, time required for the step of the chemical reaction may be at least about 10 minutes, and more specifically, this time may be designed at any time period in the range of at least about 5 minutes to at least about 15 minutes depending on the conditions desired for the chemical reaction. A chemical reaction efficiency of considerable level is generally achieved when the time is designed to be at about 10 minutes or longer.

DETAILED DESCRIPTION OF THE PREFERRED EMBODIMENTS

Next, the present invention is described in further detail by referring to preferred embodiments of the present invention.

Figure 1A:
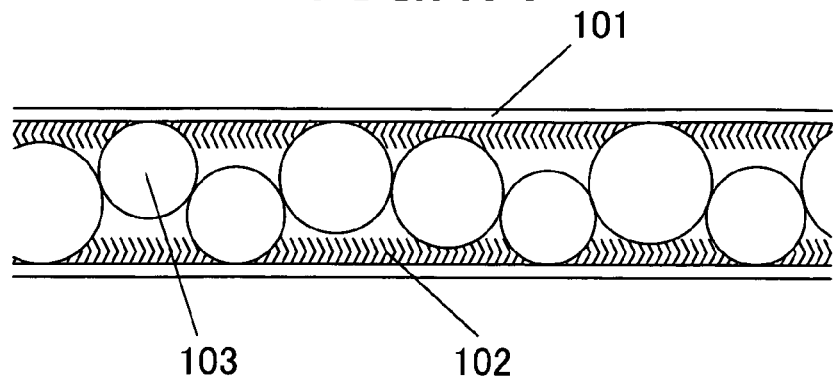
FIGS. 1A to 1C are schematic views showing the structures of the chemical reaction device and the chemical reaction system according an embodiment of the present invention.
Figure 1B:
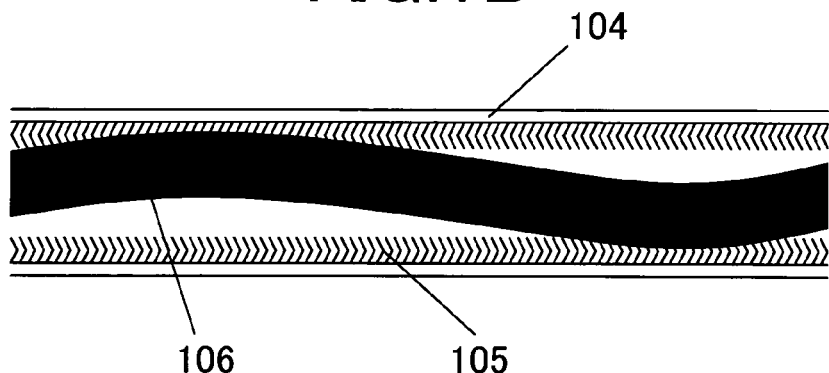
Figure 1C:
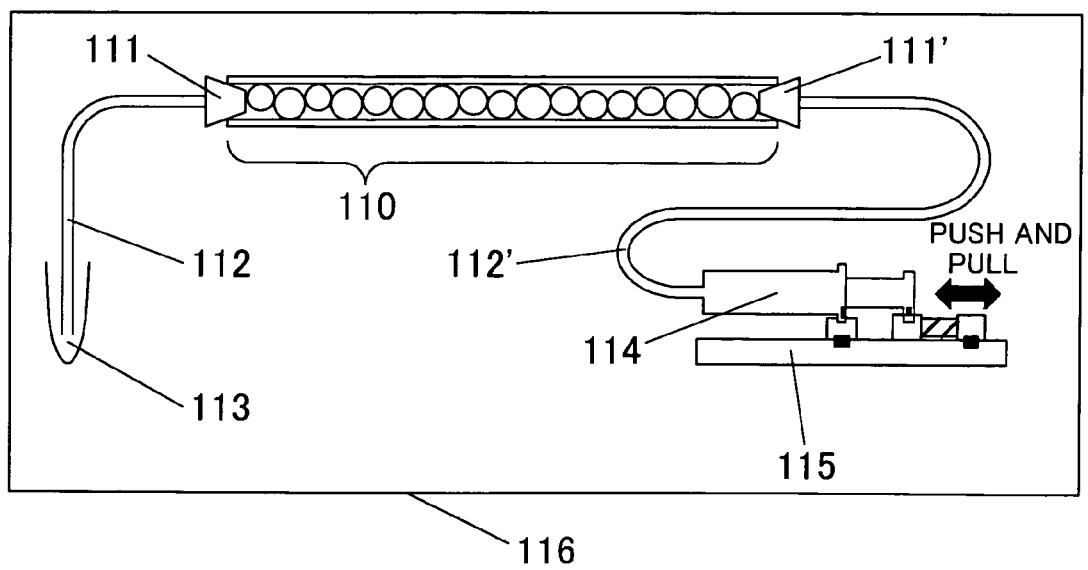

FIGS. 1A to 1C are views schematically showing the structure of the chemical reaction device and the chemical reaction system according to first embodiments of the present invention. FIG. 1A is a partial exploded view of an exemplary reaction vessel in the chemical reaction device according to an embodiment of the present invention. This reaction vessel comprises a channel defined in capillary 101 having an enzyme 102 immobilized on its interior surface and glass beads 103 filled in its interior. The glass beads 103 function as structures obstructing the flow through the interior or the lumen of the capillary 101. Enzymatic reaction can be induced by passing the reaction solution containing the molecule which is a substrate for the enzymatic reaction through the lumen of this capillary 101. This reaction vessel is applicable to a wide variety of enzymatic reactions, and the reaction vessel described herein as an example is the one having trypsin immobilized thereto used for the purpose of proteolysis. The proteolytic product produced by using this reaction vessel can be used, for example, for fingerprinting of the protein, or for identification of the unknown protein by measuring the molecular weight with a mass spectrometer. The capillary 101 having the trypsin immobilized on its interior surface can be produced, for example, by the procedure as described below. The capillary used in this embodiment is a fused quartz capillary having an inner diameter of 150 micron. First, the capillary is washed with pure water to clean the interior surface of the capillary to thereby introduce hydroxy group, and 1N aqueous solution of sodium hydroxide at 80° C. is passed through the capillary for 10 minutes, and the capillary is again washed with pure water until the pH returns neutral. Next, 1% aqueous solution of 3-aminopropyltrimethoxysiane is introduced in the capillary to introduce amino group on the interior surface of the capillary, and the reaction is allowed to proceed at room temperature for 10 minutes. The capillary is then washed with pure water, and allowed to stand in an oven at 120° C. for 60 minutes. Next, 500 mM succinic anhydride (in 1-methyl-2-pyrrolidone) is introduced in the capillary to introduce carboxyl group on the interior surface of the capillary, and the reaction is allowed to proceed 50° C. for 60 minutes. The capillary is then thoroughly washed with pure water. Next, 20 mM N-hydrosuccineimide and 100 mM N-ethyl-N'-3-methylaminopropylcarbodiimide (in 0.1M borate buffer (pH 6.2)) are introduced in the capillary to activate the carboxyl group that has been introduced on the capillary, and after leaving it at room temperature for 60 minutes, the capillary is washed with 0.1M borate buffer (pH 6.2) and pure water. Finally, 50 mg/mL trypsin (in 0.1M borate buffer (pH 6.2)) is introduced in the capillary to immobilize trypsin, and after leaving it in the refrigerator at 4° C. for one day, the capillary is washed with 10 mM Tris-HCl buffer solution (pH 8.0) Until its use, the capillary is stored at 4° C. with 10 mM Tris-HCl buffer solution (pH 8.0) filled in its interior capillary. The capillary is cut immediately before its use at an appropriate length, for example, at 20 cm, and the obstacle are filled in its interior. The obstacle used in this embodiment is glass beads 103, and more specifically, the glass beads which had passed through a 126 micron mesh sieve but which failed to pass through a 105 micron mesh, and which had been ultrasonically washed. The size of the glass beads 103 may be either consistent or inconsistent. In addition, the beads used for the obstacle may comprise a material other than glass such as a resin, and the beads may have any desired configuration such as a sphere, an ellipsoid, or a polyhedron. When the size of the beads is defined by using the term "diameter", this term refers to the diameter in the case of a sphere, the major axis in the case of an ellipsoid, and in the case of a polyhedron, the longest of the line segment extending between a point on the surface of and the point symmetrically opposite to that point in relation to the center of the polyhedron.

Alternatively, the obstacle may comprise a stainless steel wire having a diameter of about 100 microns which has been cut. FIG. 1B shows an embodiment of the reaction vessel wherein a stainless steel wire has been used for the obstacle. This reaction vessel comprises a channel wherein an enzyme 105 is immobilized on the inner surface of a capillary 104, and a stainless steel wire 106 having a diameter of 100 microns is accommodated in the interior of the capillary 104. When such wire or similar obstacle which is a strip member, cylindrical member, or the like is used, the obstacle may be configured whether it is moved by the flow of the solution or by other mechanical means.

In the case of a microparticle-filled column wherein the column is filled with the structure, and the structure comprises microparticles having a diameter of several microns which is by far smaller than the diameter of the capillary, the void where the substrate-containing solution can flow will be extremely small, and the pressure loss will be extremely high. In such a case, the flow of the solution will be a laminar flow with no considerable increase in the substantial diffusion coefficient, and the substrate will confront with the difficulty in reacting with the enzyme 102 immobilized on the interior surface, and as a consequence, the reaction efficiency will be reduced. For example, when a capillary having an inner diameter of 150 microns is used for the reaction vessel, the optimal diameter range of the beads used for the obstacle accommodated in the capillary is in the range of about 50 micron to about 130 micron so that the beads will not be too small compared to the capillary while not too big to be received by the capillary and will enable formation of the solution flow that accelerates the chemical reaction. In other words, the beads may have a diameter which is at least about 30% and at most about 90% of the diameter of the capillary, and in this case, the flow of the reaction solution formed in the capillary will not be a laminar flow but a flow in transition from the laminar flow to the turbulent flow or a turbulent flow. When the flow in the capillary is a laminar flow, a considerable time is required for the substrate to move from the center of the flow to the vicinity of the channel wall, while all molecules will be promoted to collide with the channel wall in the case of a turbulent flow or a flow in transition from the laminar flow to the turbulent flow including partial turbulent flow and the efficiency of the chemical reaction is thereby improved. In this case, the plurality of beads in the interior of the capillary may be arranged either such that the centers of the beads are aligned on a straight line or such that the centers of the beads are not aligned on a straight line as shown in FIG. 1A.

When considered on the basis of the void, namely, the ratio of the interior volume of the capillary or the channel excluding the volume of the structure (obstacle) to the entire interior volume of the capillary or the channel, namely, the ratio represented by the formula: V1/V2 when V1 is the volume of the space in the capillary where the sample can flow and V2 is the interior volume of the capillary if no structure (obstacle) were present, the void of the microparticle-filled column would be close to the void in the case of the hexagonal closest packing which is the closest packing in a free space with the void of 0.26. As described above, the flow of the solution is a laminar flow in the case of the microparticle-filled column with a low substantial diffusion coefficient, and the substrate has difficulty in reaching the enzyme 102 immobilized on the interior surface. As a consequence, the reaction efficiency will be insufficient. In the present invention, the void should be larger than that of the microparticle-filled column in order to form a flow of the solution that allows the chemical reaction, and the adequate range for the void is about 0.5 to about 0.7 in the case when beads are used for the obstacle. When the obstacle is not in the form of spheres or ellipsoids but a continuous strip as shown in FIG. 1B, design freedom of the void is significantly higher, and a void in the range of about 0.4 to about 0.95 can be provided. When the obstacle allows provision of the void of the range as described above, the flow of the reaction solution created will not be a laminar flow but a turbulent flow or a flow in a transition state from the laminar flow to the turbulent flow including partial turbulence, and the efficiency of the chemical reaction can be improved as in the case of using the beads of predetermined diameter.

FIG. 1C is a view schematically showing the structure of the entire chemical reaction system produced by using the chemical reaction device according to the first embodiment of the present invention. A reaction vessel 110 is the one described by referring to FIG. 1A comprising the capillary 101 having the enzyme 102 immobilized on its interior surface and filled with the glass beads 103. On opposite ends of the reaction vessel 110 are provided connectors 111 and 111' which prevent exit of the glass beads 103 filled in the reaction vessel 110 from the reaction vessel 110 while feeding the solution to the reaction vessel 110, and these connectors 111 and 111' also join the reaction vessel 110 with feed capillaries 112 and 112'. A sample tube 113 filled with the reaction solution containing the molecule which serves the substrate for the enzymatic reaction is provided at the end of the feed capillary 112, and a syringe 114 of a syringe pump 115 is provided at the end of the feed capillary 112'. When the syringe pump 115 is operated, the reaction solution in the sample tube 113 is introduced in the reaction vessel 110, and the reaction solution introduced subsequently moves either in one direction or back and forth in two directions corresponding to the operation of the syringe pump 115. Such operation can promote the reaction between the enzyme immobilized on the interior surface of the reaction vessel 110 and the substrate in the reaction solution. The entire reaction system may be placed in a thermal chamber 116 in order to maintain the temperature at a constant level during the chemical reaction. When the syringe 114 and the syringe pump 115 are not resistant to temperature load, the syringe 114 and the syringe pump 115 may be placed outside the thermal chamber 116. In the case of the proteolytic reaction using the trypsin-immobilized glass beads as described by referring to FIG. 1A, the sample reaction solution of about 1 μL to about 300 μL can be handled with no inconvenience. For example, when the syringe pump 115 is operated at the volume flow rate of about 1 to about 100 μL per minute, behavior of the reaction solution in the reaction vessel 110 will be a flow in transition from the laminar flow to the turbulent flow and not a laminar flow, with an increased substantial diffusion constant of the substrate molecule.

Figure 2A:
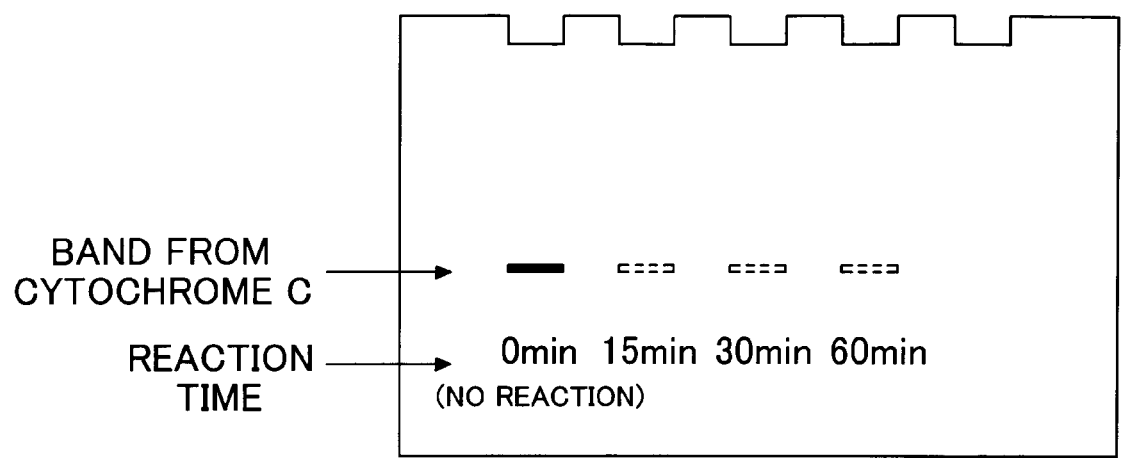
FIGS. 2A and 2B are views showing the results of electrophoresis obtained by using the chemical reaction device and the chemical reaction system according an embodiment of the present invention.
Figure 2B:
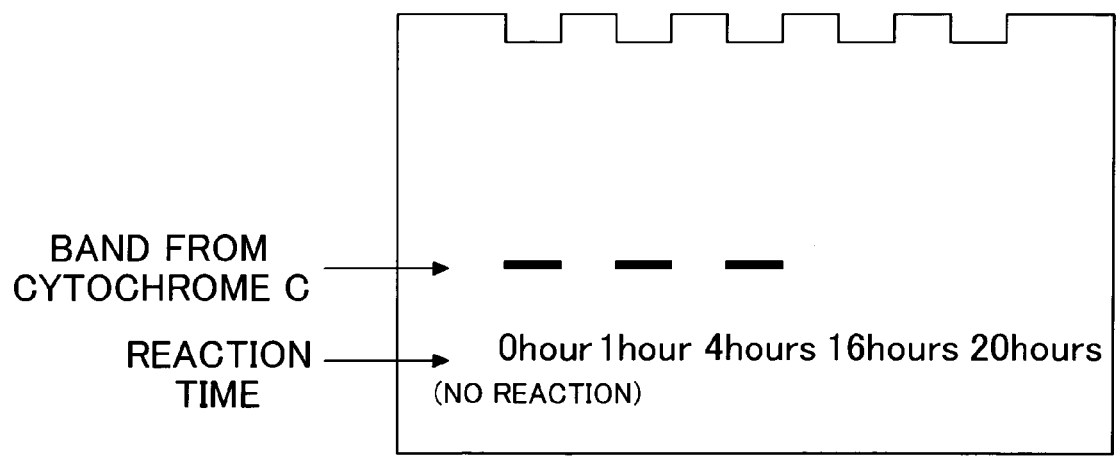

Next, the use of the system of the present invention is described. Cytochrome C, which is a protein, was decomposed in this chemical reaction system by trypsin. The reaction solution was 10 μL of 0.2 mg/mL cytochrome C (in 10 mM Tris-HCl buffer solution (pH 8.0)), and this solution was moved back and forth in the reaction vessel at a flow rate of 10 μL per minute and at a reaction temperature of 37° C. for the proteolysis by trypsin. The reaction time was 0 minute (no reaction), 15 minutes, 30 minutes, or 60 minutes. To 5 μL of the reaction solution collected after the reaction was added 2 μL of loading buffer (313 mM Tris-HCl, 10% SDS, 10% mercaptoethanol, 30% glycerol, 0.01% bromophenol blue, pH 6.8), and the mixture was heated to 95° C. for about 2 minutes. Of such mixture, 3 μL was used as a sample in the electrophoresis. The electrophoresis was conducted by using 15% polyacrylamide gel having sodium dodecyl phosphate (SDS) added thereto, and an electrophoretic buffer (25 mM Tris-HCl, 192 mM glycine, 0.1% SDS, pH 8.5). The current in the electrophoresis was set at 20 mA, and after two hours of electrophoresis, the gel was stained with Coomassie Brilliant Blue for 1 hour, and destained with 10% acetic acid–40% methanol solution for 2 hours to obtain the electropherogram. For a comparison purpose, 1 μL of trypsin solution at a concentration 1 mg/mL and 39 μL of pure water were added to 50 μL of 2 mg/mL cytochrome C (10 mM Tris-HCl solution (pH 8.5)), and the mixed solution was left in a reaction tube with no movement at 37° C. to promote the proteolytic reaction. The reaction time use was 0 hour (no reaction), 1 hour, 4 hours, 16 hours, and 20 hours. The reaction products were electrophoresed as in the case of the products obtained by using the chemical reaction system to also obtain the electropherogram. FIG. 2 shows the results of the electrophoresis when cytochrome C was decomposed with trypsin as described above. FIG. 2A shows the electropherograms obtained by using the chemical reaction system of FIG. 1, and FIG. 2B shows the results obtained by leaving the reaction solution in the reaction tube with no movement. When the chemical reaction system shown in FIG. 1 is used, the band from cytochrome C observed for the reaction time of 0 minute (no reaction) is not observed in the samples of reaction times 15 minutes, 30 minutes, and 60 minutes as shown in FIG. 2A, and this indicates that the cytochrome C has been decomposed by trypsin. While no band for the proteolytic product are observed, such absence is estimated to be due to the increased variety of fragments each comprising a reduced amount as well as due to the short length of such products. In contrast, when the reaction is promoted in the reaction tube with no solution movement, the results are substantially similar whether the reaction times is 1 hour (60 minutes) or 0 hour (no reaction) as shown in FIG. 2B. While the density of the band decreases with the increase in the reaction time indicating the progress of the decomposition by trypsin, the band does not completely disappear even after the reaction time of as long as 20 hours indicating the presence of the cytochrome C that had not been decomposed. These results indicate that proteolytic reaction of the cytochrome C by trypsin is fully completed in the case of the reaction vessel of the present invention in 15 minutes. Decomposition of the protein in a solution by trypsin generally takes one day for completion when the solution is not moved. In contrast, the reaction conducted by the method of the present invention is completed in about 10 minutes to about 20 minutes, realizing a dramatic reduction of the time required for the analysis. It is to be noted that while the chemical analysis system has been described in the foregoing for the embodiment wherein the chemical reaction conducted is an enzymatic reaction using an enzyme as the probe immobilized in the interior of the capillary, the reaction may also be the one wherein a nucleic acid is used for the probe. Exemplary molecules which may be immobilized in the reaction vessel include biological molecules other than such enzyme and nucleic acid, and exemplary analytes include nucleic acids, proteins, and other biological molecules. When the chemical reaction carried out is an enzymatic reaction, the reaction that had undergone the enzymatic reaction is, for example, recovered from the capillary. When the chemical reaction carried out is the binding to the probe of the substance which is specific to the probe, the specific substance that became bonded to the probe is collected or detected after the reaction.

Compared to the case wherein the molecule involved in the chemical reaction is immobilized on the glass beads or other obstacles, the present invention wherein the molecule is immobilized on the interior surface of the reaction vessel is more tolerant to the operation that may cause damages to the molecule-immobilized surface such as introduction of the molecule-immobilized glass beads into the reaction vessel, and ease of the handling of the beads is thereby realized. This enables production of the reaction system at a reduced cost and at improved reproducibility. Another problem is the peeling or separation of the immobilized molecule induced by the flow of the reaction solution at the surface of the obstacle such as glass beads having a curved surface, and as a matter of fact, the molecule immobilized on a curved surface receive a force larger than the molecule immobilized on the non-curved surface like the interior surface of the channel (or capillary), and the molecule involved in the reaction that is immobilized on the surface is relatively easily peeled off the surface in the case of a curved surface. This is always a serious problem when the molecule is immobilized by using the physical adsorption, namely, by utilizing the adsorption caused by intermolecular force. While immobilization of the molecule using physical adsorption is quite useful due to the simple procedure, no covalent bond is present between the solid phase and the immobilized molecule in the case of the physical adsorption, and accordingly, the molecule immobilized by the physical adsorption cannot endure the physical load applied to the molecule by the fluid and the like and the molecule is liable to become peeled off the surface. However, in the case of the present invention, the molecules are immobilized in a manner resistant to the peeling in the reaction process, and a high reaction efficiency is thereby realized.

Figure 3A:
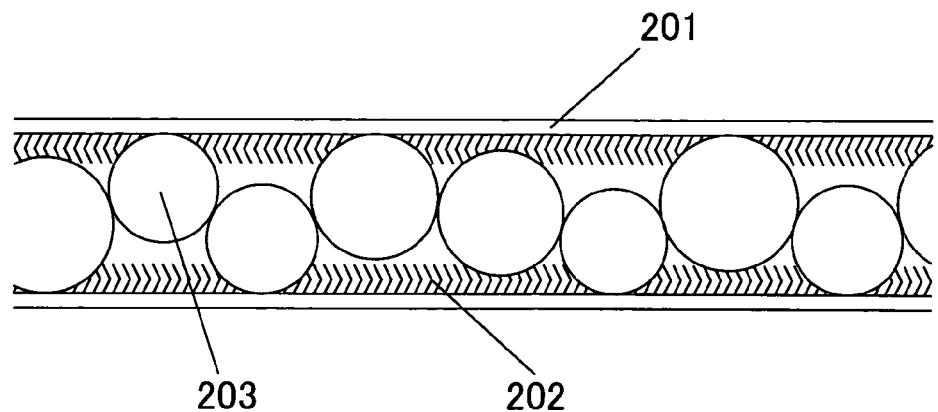
FIGS. 3A and 3B are schematic views showing chemical reaction devices for comparison with the chemical reaction device according an embodiment of the present invention.
Figure 3B:
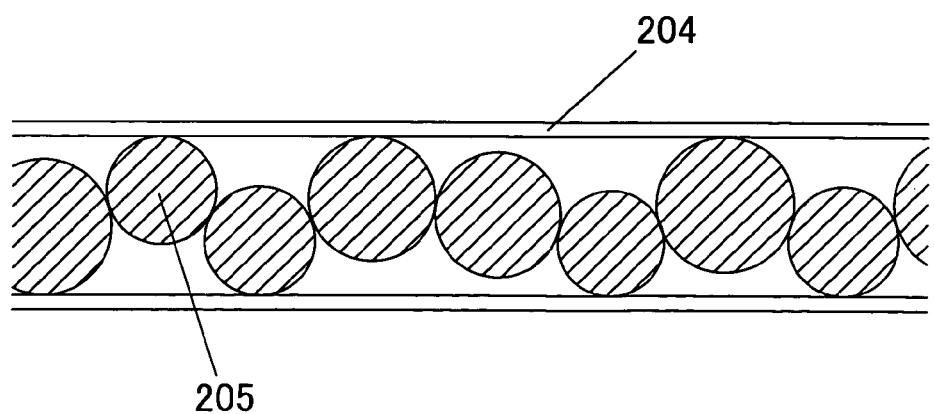

An experiment was conducted to evaluate the liability of the immobilized molecule to become peeled off the surface when the molecule is immobilized by physical adsorption. The system used was the one the same as the one shown in FIG. 1C except that the enzyme was immobilized on the interior surface of the capillary. Shown in FIG. 3 are schematic views of the chemical reaction devices wherein the molecule has been immobilized by physical adsorption. FIG. 3A is a partial exploded view of the channel of the chemical reaction devices wherein an enzyme has been immobilized by physical adsorption on the interior surface of the capillary. An enzyme 202 is immobilized on the interior surface of the capillary 201 by physical adsorption, and glass beads 203 are accommodated in the interior of the capillary 201 as an obstacle for the flow. FIG. 3B is a partial exploded view of the channel of the chemical reaction devices wherein the enzyme has been immobilized not on the interior surface of the capillary but on the glass beads by physical adsorption. In this experiment, the chemical reaction devices are produced by immobilizing trypsin as an exemplary enzyme. The immobilization of trypsin on the surface of the solid phase is carried out, for example, by the procedure as described below. In the case when trypsin is immobilized on the interior surface of the capillary 201 as shown in FIG. 3A, the capillary is first washed with pure water, and the 1N aqueous solution of sodium hydroxide at 80° C. is passed through the capillary for 10 minutes, and the capillary is again washed with pure water until the pH returns to neutral. A hydroxyl group is introduced on the interior surface of the fused quartz capillary by the treatment with the sodium hydroxide, and the surface assumes negative charge. Next, 1 mg/mL solution of trypsin in 0.05M Tris buffer solution (pH 7.0) is passed through the capillary for 1 hour at room temperature, and the capillary is washed with 0.05M Tris buffer solution (pH 7.0). Since trypsin has a calculated isoelectric point of about 8.5, it assumes a positive charge in the solution of pH 7.0, and as a consequence, it becomes immobilized on the glass surface by physical adsorption. The thus produced capillary may be stored until its use by filling 0.05M Tris buffer solution (pH 7.0) in the interior of the capillary and maintaining at 4° C. The chemical reaction device of FIG. 3A can be readily produced immediately before its use by cutting the capillary at an appropriate length and the accommodating the glass beads in the interior. The glass beads having the enzyme immobilized by physical adsorption may also be produced by using the similar reaction conditions to thereby immobilize the enzyme on the surface of the glass beads. The reaction vessel schematically shown in FIG. 3B can be produced by filling the glass beads 205 in the capillary 204. Each of the thus produced two reaction vessels is placed as a component in the chemical reaction system of FIG. 1B produced by using the same components as the first embodiment as described above except for the capillary and the glass beads, and protein-free Tris buffer solution (pH 7.0) is passed through the reaction vessel to thereby measure the amount of the trypsin remaining in the reaction vessel after the passage. The buffer solution is used at an amount of 100 μL, and the buffer solution is passed back and forth through the reaction vessel at a flow rate of 50 μL per minute. Amount of the trypsin that was peeled off into the buffer solution is measured by varying the time of the buffer reciprocal cycle. In view of the difficulty of the quantitative protein evaluation at a minute amount, trypsin labeled with a radioisotope $C^{13}$ was used in this evaluation. First, amount of trypsin that had been immobilized is determined by measuring the radiation from the trypsin solution used for the immobilization before and after the trypsin immobilization, and calculating the difference in the amount of the trypsin. The radiation of the buffer solution that had passed through the capillary is then measured to determine the amount of trypsin in the buffer solution that had been incorporated by the peeling of the trypsin. This amount was compared with the amount of the previously calculated immobilized trypsin.

Figure 4:
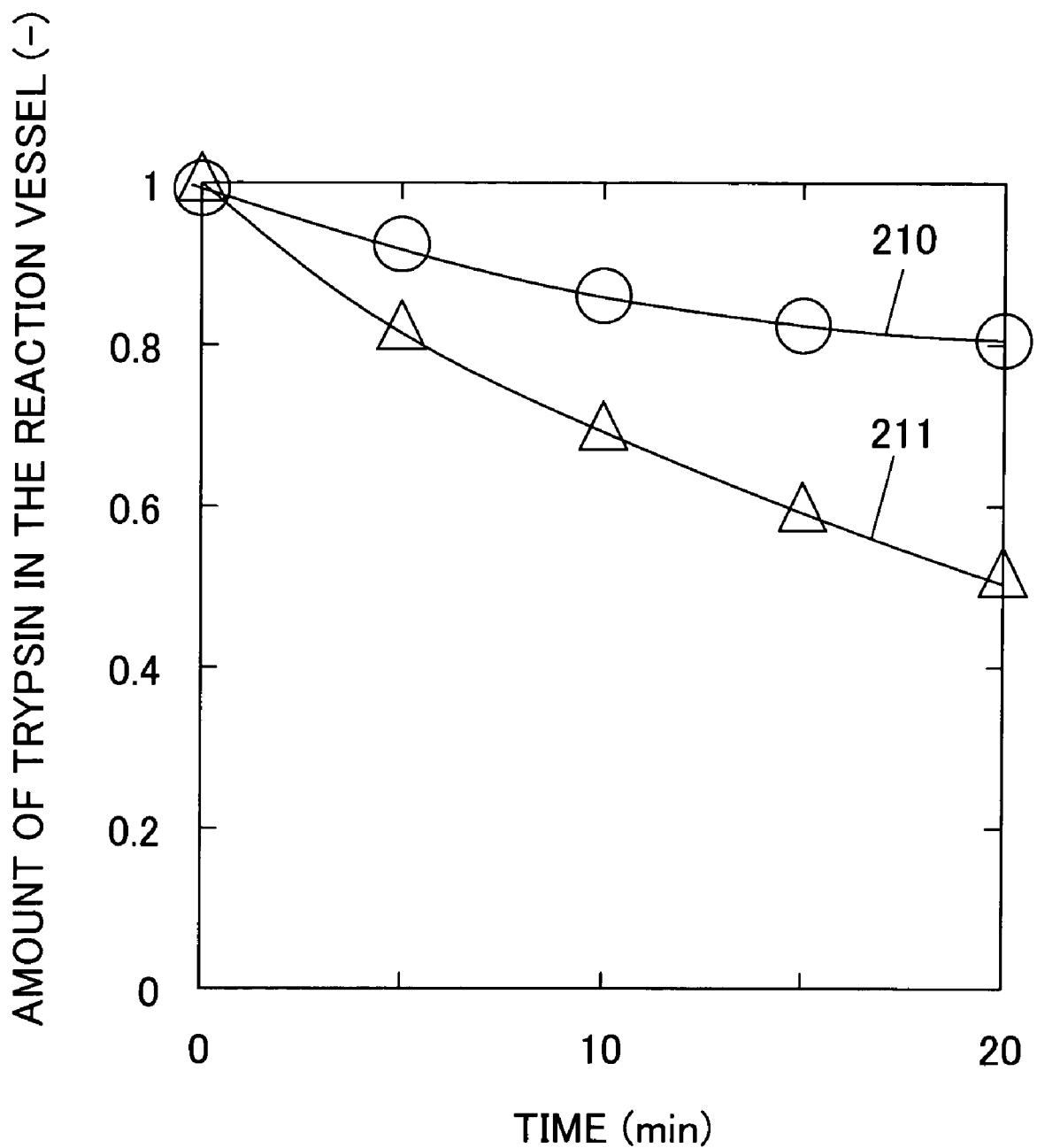
FIG. 4 is a graph showing an amount of the immobilized enzyme remaining in the chemical reaction device according to an embodiment of the present invention and the comparative chemical reaction device in relation to elapsed time.

FIG. 4 is a graph showing the time course of the amount of the immobilized trypsin remaining in the chemical reaction device, and the value has been normalized by taking the amount of trypsin that had been initially immobilized in each chemical reaction device as "1". The curve indicated with blank circle 210 represents the data of the chemical reaction device of FIG. 3A comprising the capillary 201 having the enzyme 202 being immobilized on its interior surface and the glass beads 203 filled therein, and the curve indicated with blank triangle 211 represents the data of the chemical reaction device of FIG. 3B comprising the capillary 204 filled with the enzyme-immobilized glass beads 205. For example, when the reaction time is 20 minutes, about 80% and about 50% of the trypsin are remaining in each chemical reaction device, and this indicates that a higher reaction efficiency is realized in the chemical reaction device having the enzyme 202 immobilized on the interior surface of the capillary 201 with the greater amount of effective trypsin. Although the data has been presented for the device wherein the molecule has been immobilized by utilizing physical adsorption, the situation is similar for the case when the molecule is immobilized by means of covalent bond, and higher reaction efficiency is realized when the enzyme is immobilized on the interior surface of the capillary. It is also to be noted that, when the results shown in FIGS. 2 and 4 are taken into consideration, the time of the chemical reaction should be set at any time between at least about 5 minutes and at least about 15 minutes, since the chemical reaction should proceed to the sufficient level, and simultaneously, the starting of the reaction efficiency loss by the peeling of the immobilized molecule should be considered. A chemical reaction efficiency of predetermined level is generally realized when a time of about 10 minutes is allowed for the chemical reaction.

Furthermore, when the enzyme is immobilized on the microparticles and the microparticles are suspended in a solution containing the substrate molecule for the chemical reaction, full suspension of the microparticles in the solution is generally difficult. In other words, it is difficult to bring the microparticles in full contact with the substrate molecule included in the solution to induce the chemical reaction. In addition, in use of a column filled with enzyme-immobilized microparticles, the microparticles are filled at a high rate in the reaction vessel with insufficient void as described above, and the reaction solution can only flow at a slow speed and the flow will be a laminar flow with reduced substantial diffusion speed. As a consequence, an increase in the reaction efficiency is difficult, and a high pressure pump will be required if the flow rate were to be increased. In contrast, the present invention comprises a device wherein a particular substance is immobilized on the interior surface of the reaction vessel so that the molecule reacting with the particular substance is forced to pass through a narrow space, and at the same time, wherein the flow formed is not a laminar flow and turbulent flow is at least partly induced, thereby enabling a highly efficient reaction to take place in a short time. Furthermore, since the reaction vessel of the present invention is constituted such that the reaction vessel has the particular substance immobilized on its interior surface and a structure or an obstacle accommodated in the interior as described above, the reaction vessel also enjoys the merit of reduced peeling or separation of the immobilized molecule from the surface to which it has been immobilized, which has been a serious problem in the system where the molecule is immobilized on the microparticles.

Figure 5A:
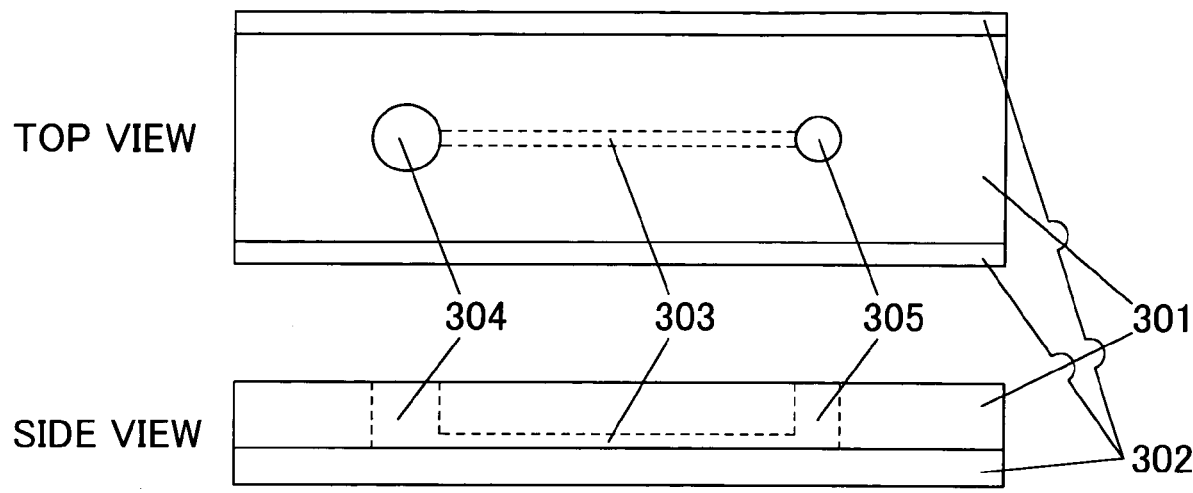
FIGS. 5A and 5B are schematic views showing the structures of the chemical analysis devices according an embodiment of the present invention.
Figure 5B:
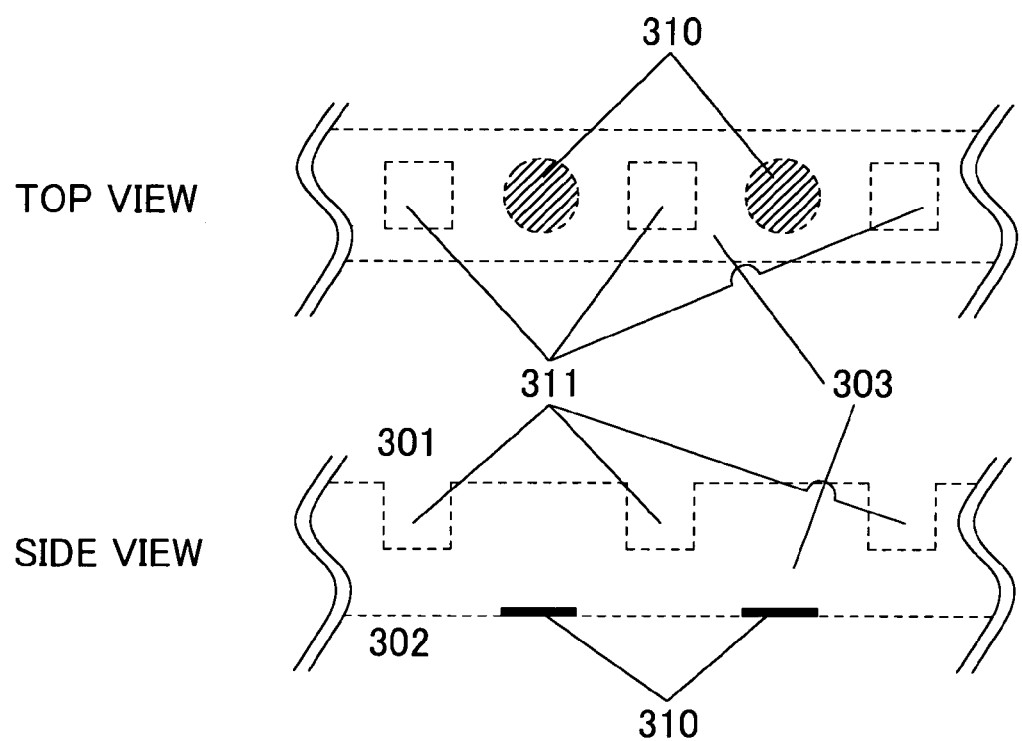

FIG. 5 schematically shows the structure of the chemical analysis device according to the second embodiment of the present invention. FIG. 5A is a total view of DNA measurement device in the form of a chip. This device comprises a flat slide glass 302 and a polydimethylsiloxane (PDMS) substrate 301 adhered to the slide glass 302, and the PDMS substrate 301 has a channel 303 formed therein to provide the site of the chemical reaction and simultaneously, the site of the detection. The slide glass 302 has a size of 25 mm×75 mm, and a thickness of about 1 mm. A nonfluorescent product comprising crown glass was used for the slide glass 302 for the subsequent fluorometric measurement. The PDMS substrate 301 has a thickness of about 2 mm, and it covers the slide glass 302 except for the margin of about 2 mm along the long sides of the slide glass 302. The regions of the slide glass 302 not covered by the PDMS substrate 301 are used as the gripper region for holding the device while it is inserted in the DNA chip scanner in the subsequent fluorometric measurement. The channel 303 has a cross section with the size of 150 micron×150 micron and the length of 4 cm. The channel 303 is formed at one end with a solution inlet 304 for introducing an analyte sample solution and washing solution, and at the other end with a connection port 305 used for connection with an outer pump which is used to introduce the solution and to pass the solution back and forth in the channel. This device is produced by the procedure described, for example, in Electrophoresis, 22, 328-33 (2001) by pouring unreacted PDMS in the mold produced by photolithographic means having the shape of the resulting PMDS substrate for curing, releasing the cured PDMS substrate 301 from the mold, and adhering the PDMS substrate 301 with the slide glass 302. FIG. 5B is an exploded view of a part of the channel 303 which functions as the chemical reaction site as well as the measurement site of shown in FIG. 5A. The channel 303 is defined between the PDMS substrate 301 and the slide glass 302. PDMS substrate 301 has projections 311 which protrude into the channel 303 from the upper side of the channel 303. This projection 311 has the effect of disturbing the flow of the reaction solution to increase the substantial diffusion coefficient of the substrate. Beside the fact that an excessively thin structure is difficult to provide on the PDMS substrate 301, the structure should have a substantial size to create turbulence in the flow of the solution passing through the channel 303 to thereby increase the reaction speed. An adequate size contemplated for the projection is at least about 1/3 of the width or the height of the channel. In the example shown in FIG. 3B, the projection 311 is a cube with the length of sides of 75 microns. The projections 311 are disposed at an interval of 200 microns. In this example, a DNA probe 310 is spotted on the side of the slide glass 302 of the channel 303. While the spots are not limited for their size, the spot typically has a diameter of about 50 microns to about 100 microns. The spotting of the DNA probe 310 may be conducted by using a commercially available spotter. The spotting of this DNA probe on the slide glass 302 may be completed before the adhesion of the PDMS substrate 301 to the slide glass 302. DNA probes 310 are provided at an interval of 200 micron as in the case of the projections 311.

Figure 6A:
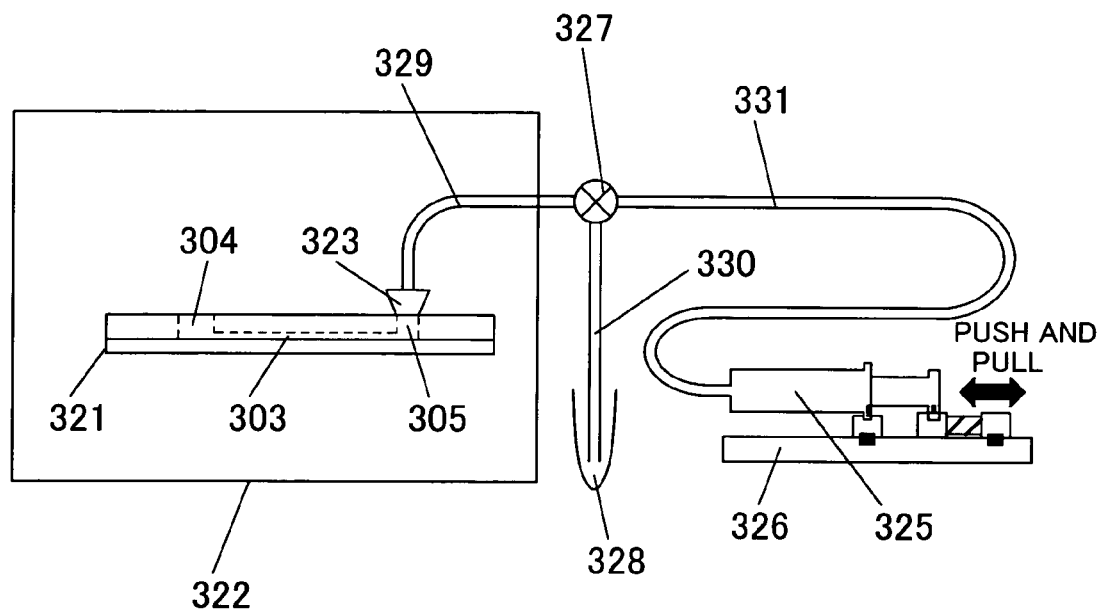
FIGS. 6A and 6B are schematic views of the chemical analysis system according to an embodiment of the present invention.
Figure 6B:
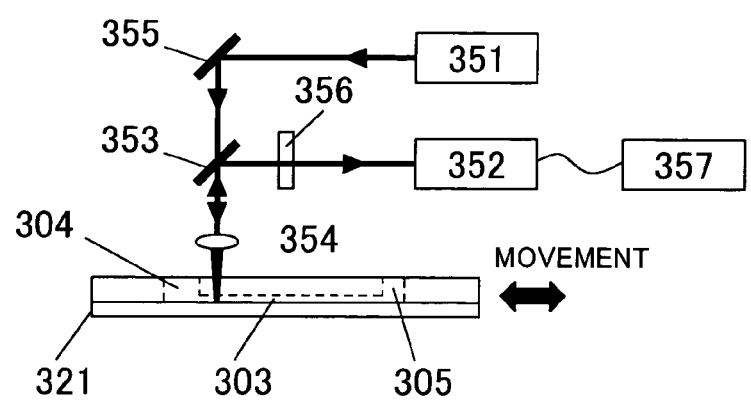

FIG. 6 is a view schematically showing the constitution of the chemical analysis system wherein the DNA measurement device of FIG. 5 has been incorporated. The DNA measurement device 321 having the solution inlet 304 for introducing the analyte sample solution and the washing solution, the channel 303, and the connection port 305 is accommodated in the thermal chamber 322. To the connection port 305 is connected to a connection capillary 329 by the intervening connector 323. The connection capillaries 329, 330, and 331 are divided by a three way valve 327 into three sections. A capillary section 331 is connected at one end with a syringe 325 on a syringe pump 326, and a capillary section 330 is at one end connected to waste reservoir 328. In analyzing DNA, the analyte fluorescence-labeled target DNA is captured by a DNA probe by means of hybridization which is a type of chemical reaction, and the captured fluorescence-labeled target DNA is measured by fluorescence, as in the case of the normal DNA chip. This fluorometric measurement may be accomplished by various methods such as those using a fluorescence microscope. An embodiment using a system like a DNA chip scanner is shown in FIG. 6B. The beam exiting from a laser 351 is reflected at a dichroic mirror 355, passes through a dichroic mirror 353, and condensed by a lens 354 to be directed to the DNA measurement device. The fluorescence produced by fluorescence-labeled target DNA upon irradiation of the fluorescence-labeled target DNA with the laser beam is condensed by the lens 354, reflected by the dichroic mirror 353, passes through an optical filter 356, and measured by a photomultiplier 352 for analysis by a personal computer 357. In order to conduct the measurement for each DNA probe in the DNA measurement device, laser beam scanning may be carried out by moving the DNA measurement, or by constituting the scanner-like system as described above so that a part of the system is movable and moving this movable part of the system. It is to be noted that the scanner-like system similar to this system can be used in the embodiments shown in FIGS. 1A, 1B, and 1C. To be more specific, in the embodiments shown in FIGS. 1A, 1B, and 1C, when the chemical reaction is the binding between a probe and a substance which specifically reacts with the probe, the fluorescence emitted by the fluorescence label which is directly or indirectly bonded to the probe can be detected by the system like the one shown in FIG. 6B after removing the structure such as beads or the wire accommodated in the capillary after the completion of the reaction.

An embodiment of DNA analysis using the DNA measurement device 321 was conducted. The DNA probes used were synthetic DNAs having a length of 18 bases which is a part of the nucleotide sequence on the antisense side of the exons of p53 (Exons 1 and 3 were not used; 10 types in total; designated probes 1 to 10). The target DNAs used were synthetic DNAs having a length of 18 bases which are fully complementary to the DNA probes, and which are labeled with Cy3 fluorescence marker (10 types in total, target 1 to 10). The melting temperature of the complementary DNA probe and the target DNA was about 70° C. The sequences are as described below.

```
Sequence of DNA probe 1:
5'-TGTCACCGTCGTGGAAAG-3'        (SEQ ID NO: 1)

Sequence of DNA probe 2:
5'-ATCTGACTGCGGCTCCTC-3'        (SEQ ID NO: 2)

Sequence of DNA probe 3:
5'-AAGAAGCCCAGACGGAAA-3'        (SEQ ID NO: 3)

Sequence of DNA probe 4:
5'-GCCTCACAACCTCCGTCA-3'        (SEQ ID NO: 4)
```

-continued

```
Sequence of DNA probe 5:
5'-TCATAGGGCACCACCACA-3'        (SEQ ID NO: 5)

Sequence of DNA probe 6:
5'-ATGATGGTGAGGATGGGC-3'        (SEQ ID NO: 6)

Sequence of DNA probe 7:
5'-CCCTTTCTTGCGGAGCTT-3'        (SEQ ID NO: 7)

Sequence of DNA probe 8:
5'-TTTCTTCTTTGGCTGGGG-3'        (SEQ ID NO: 8)

Sequence of DNA probe 9:
5'-CCTGGGCATCCTTGAGTT-3'        (SEQ ID NO: 9)

Sequence of DNA probe 10:
5'-ATGGCGGGAGGTAGACTG-3'        (SEQ ID NO: 10)

Sequence of DNA target 1:
5'-CTTTCCACGACGGTGACA-3'        (SEQ ID NO: 11)

Sequence of DNA target 2:
5'-GAGGAGCCGCAGTCAGAT-3'        (SEQ ID NO: 12)

Sequence of DNA target 3:
5'-TTTCCGTCTGGGCTTCTT-3'        (SEQ ID NO: 13)

Sequence of DNA target 4:
5'-TGACGGAGGTTGTGAGGC-3'        (SEQ ID NO: 14)

Sequence of DNA target 5:
5'-TGTGGTGGTGCCCTATGA-3'        (SEQ ID NO: 15)

Sequence of DNA target 6:
5'-GCCCATCCTCACCATCAT-3'        (SEQ ID NO: 16)

Sequence of DNA target 7:
5'-AATCTCCGCAAGAAAGGG-3'        (SEQ ID NO: 17)

Sequence of DNA target 8:
5'-CCCCAGCCAAAGAAGAAA-3'        (SEQ ID NO: 18)

Sequence of DNA target 9:
5'-AACTCAAGGATGCCCAGG-3'        (SEQ ID NO: 19)

Sequence of DNA target 10:
5'-CAGTCTACCTCCCGCCAT-3'        (SEQ ID NO: 20)
```

Figure 7:
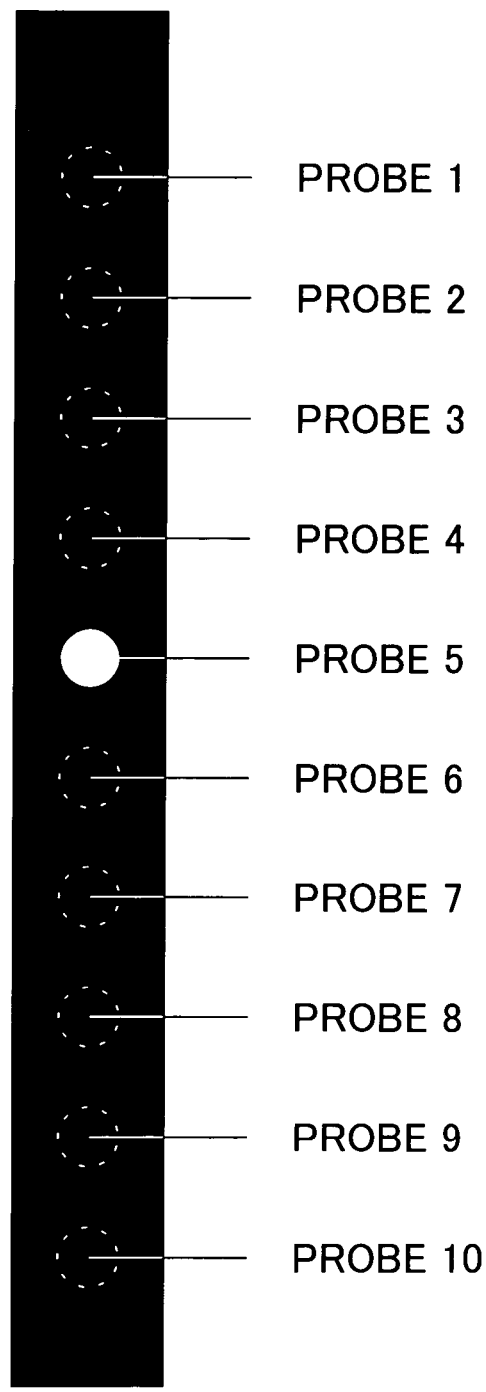
FIG. 7 is a view showing the result of fluorometric analysis obtained by using the chemical analysis device according an embodiment of the present invention.

Immobilization of the DNA probe can be accomplished by various methods. In this embodiment, the DNA probe was immobilized by using a spotter, and the DNA probe solution was spotted on a slide glass coated with poly-L-lysine by the tip of a spotter. The DNA probes were spotted in a line from the side of the solution inlet 304 to the side of the connection port 305 in the order of from DNA probe 1 to DNA probe 10. After the spotting, the slide glass was exposed to steam for several seconds for rehydration, and the DNA probe was immobilized by irradiating with UV of 60 mJ in a UV cross linker. In order to prevent non-specific hybridization, the slide glass was immersed in a blocking solution for 20 minutes, and washed with pure water and ethanol in this order. The blocking solution was prepared by mixing 335 mL of 1-methyl-2-pyrrolidone, 5.5 g of succinic anhydride, and 15 mL of 1M sodium borate (pH 8.0). The hybridization buffer solution used was 4×SSC–0.1% SDS solution, and the solution was prepared so that concentration of the target DNA was $1\times10^{-10}$M. Immediately before the analysis, the sample solution containing the target DNA was heated to 94° C. for 2 minutes for denaturation, and the solution was cooled on ice. The analysis was conducted by the procedure as described below. First, the thermal chamber 322 was set at 45° C., and left at this temperature for 10 minutes for stabilization. Next, 10 μL of the sample solution that had been kept on ice was introduced into the solution inlet 304. The three way valve 327 was opened in the direction to communicate the syringe 325 and the connection port 305, and the syringe pump 326 was operated to introduce and pass the sample solution to and through the channel 303 having the DNA probes spotted therein. Since the channel 303 has an interior volume of up to 1 μL, the sample solution that had been introduced in the channel 303 passes through the connection port 305 to become introduced in the capillary 329. The syringe pump 326 was stopped when the syringe 325 has moved 10 μL which is the volume identical with the volume of the sample. The capillary 329 between the three way valve 327 and the connection port 305 was designed to have an interior volume exceeding 10 μL so that the sample solution would not reach the three way valve 327. The piston of the syringe 325 was moved back and forth by the syringe pump 326 to move the sample solution back and forth in the channel 303 having the DNA probe immobilized therein to thereby promote the hybridization. In this embodiment, the volumetric flow rate was 10 μL per minute. It is important that the volumetric flow rate used is determined so that a turbulent flow is at least partly induced in the channel 303 by the projection (the projection 311 described for FIG. 5), and the hybridization is accelerated by a turbulent flow which assists reaching of the target DNA to the DNA probe. After reacting for 10 minutes, the sample solution is pulled to the side of the syringe 325 past the three way valve 327, and the three way valve 327 was turned to connect the syringe 325 and the waste reservoir 328 to discard the sample solution that had undergone the reaction in the waste reservoir 328. Next, the system was washed with 30 μL of 1×SSC–0.03% SDS solution, 30 μL of 0.2×SSC, 30 μL of 0.05×SSC, and 30 μL of pure water. The washing was conducted by supplying the washing solution in a procedure similar to the washing except that the volumetric flow rate of the washing solution was increased to 30 μL per minute, washing time was 1 minute, and the solution was subsequently discarded in the waste reservoir 328. The temperature during the washing was 45° C. which is lower than the melting temperature, and most of the target DNA that had been captured on the DNA probe by the specific hybridization endured the peeling and remained on the surface. After the washing, the DNA measurement device 321 was collected from the thermal chamber 322, and fluorescence was measured by a DNA chip scanner. The slide glass and the PDMS resin which had been used for producing the DNA measurement device was substantially transparent to visible light and did not emit the fluorescence, and therefore, the target Cy3 fluorescence was not interfered. FIG. 7 schematically shows the results of the scanning of the DNA measurement device 321 after the reaction with the DNA chip scanner in an exploded view of the part of the channel 303. The results shown in FIG. 7 is the analysis of the sample solution which only contain target 5. Fluorescence was observed only for spot where probe 5 complementary to target 5 had been spotted while no fluorescence was observed for other spots (indicated by white dotted line) of the probe other than the probe 5, indicating that the results observed reflected hybridization that depended on sequences. As described above, hybridization reaction which is generally a time-consuming step could be accomplished in about 10 minutes by providing a projection as the structure near the DNA probe in the channel and inducing a turbulent flow in the flow of the sample.

In this embodiment, a combination of PDMS resin and a slide glass for the material was used in producing the device. The device can be also produced by adhering a glass component with another glass component, or by using other resins (for example, polymethyl methacrylate). In addition, surface irregularities of various configurations in the channel can be utilized in addition to the simple repetition of cubic projections. Since the turbulent flow occurs in the vicinity of the structure, the distance between the site of spotting the DNA probe and the structure is critical. Since the distance required for the formation of the established flow in the case of a simple channel is believed to be a distance about several folds of the width of the channel, the distance between the center of the spot of the DNA probe and the center of the structure in the direction of the solution flow is preferably designed to be up to about threefold the width of the channel in the plane substantially perpendicular to the direction of the solution flow, namely, the height or distance between the interior surface of the channel where the spot has been provided and the opposite interior surface of the channel. Alternatively, glass beads and other obstacles may be accommodated in the channel having the DNA probe immobilized therein instead of providing a structure in the channel as in the case of the first embodiment to thereby cause a turbulent flow in the flow of the solution to thereby increase the hybridization speed. The fluorescence can also be directly measured in this case with an optical means such as a DNA chip scanner if the obstacles are optically substantially transparent, and if not substantially transparent, the obstacles may be removed after the reaction and before the measurement. While the DNA measurement device described in this embodiment has been a chemical analysis system wherein a DNA is used for the prove to measure the DNA, an immunoanalysis utilizing an antibody or like may also be carried out, and the molecule immobilized may comprise proteins other than the nucleic acid or the antibody. The analyte may also comprise a nucleic acid, a protein, and a biological molecule. While the molecule measured in this embodiment is the captured molecule, a chemical analysis device utilizing an enzyme sensor, for example, is also contemplated wherein the product of the specific reaction between the immobilized enzyme and the analyte molecule is detected in another region in the downstream. While the captured molecule is detected by using fluorometry, a highly sensitive chemical analysis system can also be constituted by using measurements such as chemiluminescence, color reaction, and surface plasmon scattering.

The present invention has realized a chemical reaction device, a chemical reaction system, and a chemical reaction method which exhibit high reaction efficiency as well as high sample throughput. The present invention has also realized a chemical reaction device, a chemical reaction system, and a chemical reaction method which are useful when the reaction should be completed in a short time and the number of the target molecule is small. The present invention has also realized a chemical reaction device, a chemical reaction system, and a chemical reaction method which are highly sensitive.

What is claimed is:

1. A chemical reaction device, comprising
   a capillary having defined therein a channel for receiving a solution, and
   at least a structure placed inside of said channel, wherein
   at least a particular molecule which is chemically reactive with at least a substance in said solution is immobilized on an interior surface of said channel, wherein said structure has a diameter which is in a range of 30 to 90% of a diameter of said channel.

2. The chemical reaction device according to claim 1, wherein, when volume allowed for a sample to flow in said channel is V1, interior volume of said channel is V2, and the ratio V1/V2 is in a range of 0.4 to 0.95.

3. The chemical reaction device according to claim 1, wherein said structure is a fine particle or a strip.

4. The chemical reaction device according to claim 1, wherein said structure is a plurality of fine particles arranged in said channel such that their centers are not aligned on one straight line.

5. The chemical reaction device according to claim 1, wherein a flow of said solution in said channel is at least a partly turbulent flow.

6. The chemical reaction device according to claim 1, wherein said particular molecule immobilized on the interior surface of said channel is a nucleic acid or a protein.

7. The chemical reaction device according to claim 1, wherein said channel is defined by a groove formed in a first substrate and a second substrate disposed to cover said groove.

8. The chemical reaction device according to claim 1, wherein said channel is a lumen of a capillary.

9. The chemical reaction device according to claim 1, wherein
   said particular molecule is immobilized on at least an immobilization area in said channel, and
   a distance in a flow direction of said solution between a center of said structure and a center of said immobilization area is up to about threefold a width of the channel in a plane substantially perpendicular to said solution flow direction.

10. The chemical reaction device according to claim 1, wherein said structure is a material that fills an interior of the channel in the capillary to obstruct flowing of said solution so as to promote turbulent flow therein.

* * * * *

UNITED STATES PATENT AND TRADEMARK OFFICE
CERTIFICATE OF CORRECTION

PATENT NO. : 7,666,662 B2  Page 1 of 1
APPLICATION NO. : 10/854018
DATED : February 23, 2010
INVENTOR(S) : Kohara et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 876 days.

Signed and Sealed this

Seventh Day of December, 2010

David J. Kappos
*Director of the United States Patent and Trademark Office*